(12) United States Patent
Colella et al.

(10) Patent No.: US 11,402,369 B2
(45) Date of Patent: Aug. 2, 2022

(54) CUVETTE-BASED APPARATUS FOR BLOOD COAGULATION MEASUREMENT AND TESTING

(71) Applicant: Instrumentation Laboratory Company, Bedford, MA (US)

(72) Inventors: Gregory M. Colella, Montclair, NJ (US); Henry D. Huang, Edison, NJ (US); Anthony F. Kuklo, Jr., Bridgewater, NJ (US); Dimitri Shishkin, Whippany, NJ (US); Maria Figueroa, Elizabeth, NJ (US); James A. Mawhirt, Brooklyn, NY (US)

(73) Assignee: INSTRUMENTATION LABORATORY COMPANY, Bedford, MA (US)

( * ) Notice: Subject to any disclaimer, the term of this patent is extended or adjusted under 35 U.S.C. 154(b) by 274 days.

(21) Appl. No.: 16/805,375

(22) Filed: Feb. 28, 2020

(65) Prior Publication Data

US 2020/0200731 A1 Jun. 25, 2020

Related U.S. Application Data

(63) Continuation of application No. 16/210,433, filed on Dec. 5, 2018, now Pat. No. 10,578,605, which is a
(Continued)

(51) Int. Cl.
*G01N 35/00* (2006.01)
*G01N 33/49* (2006.01)
*B01L 3/00* (2006.01)

(52) U.S. Cl.
CPC ...... *G01N 33/4905* (2013.01); *B01L 3/50273* (2013.01); *B01L 3/502715* (2013.01);
(Continued)

(58) Field of Classification Search
CPC ......... Y10T 436/10; Y10T 436/101666; Y10T 436/108331; Y10T 436/11; Y10T 436/25;
(Continued)

(56) References Cited

U.S. PATENT DOCUMENTS 4,497,774 A 2/1985 Scordato
5,154,082 A 10/1992 Mintz
(Continued)

FOREIGN PATENT DOCUMENTS

WO 97/24604 A1 7/1997

OTHER PUBLICATIONS

Supplemental European Search Report for EP Application No. 09798718.4, dated Jul. 24, 2012, 11 pgs.

*Primary Examiner* — Dean Kwak
(74) *Attorney, Agent, or Firm* — Burns & Levinson LLP (57) ABSTRACT

An apparatus for measuring blood clotting time includes a blood clot detection instrument and a cuvette for use with the blood clot detection instrument. The cuvette includes a blood sample receptor-inlet; a channel arrangement including at least one test channel for performing a blood clotting time measurement, a sampling channel having at least one surface portion that is hydrophilic, communicating with the blood sample receptor-inlet and the at least one test channel, and a waste channel having at least one surface portion that is hydrophilic, communicating with the sampling channel; and a vent opening communicating with the sampling channel. The sampling channel, the vent opening and the waste channel, coact to automatically draw a requisite volume of a blood sample deposited at the blood receptor-inlet, into the sampling channel. More specifically, air compressed within the blood clot detection instrument, the at least one test channel of the cuvette, and the section of the sampling channel extending beyond the vent opening of the cuvette,
(Continued)

coacts with the waste channel to cause a leading edge of the blood sample drawn into the sampling channel from the blood receptor-inlet, to pull back within the sampling channel and uncover an optical sensor in of the blood clot detection instrument. The uncovering of the optical sensor activates a pump module of the blood clot detection instrument, which draws the requisite volume of the blood sample into the at least one test channel.

12 Claims, 6 Drawing Sheets

Related U.S. Application Data continuation of application No. 13/959,007, filed on Aug. 5, 2013, now Pat. No. 10,180,419, which is a continuation of application No. 13/474,243, filed on May 17, 2012, now abandoned, which is a continuation of application No. 12/503,665, filed on Jul. 15, 2009, now abandoned.

(60) Provisional application No. 61/081,290, filed on Jul. 16, 2008.

(52) U.S. Cl.
CPC ... *B01L 3/502723* (2013.01); *B01L 3/502746* (2013.01); *B01L 2200/12* (2013.01); *B01L 2200/146* (2013.01); *B01L 2200/16* (2013.01); *B01L 2300/027* (2013.01); *B01L 2300/0654* (2013.01); *B01L 2300/0816* (2013.01); *B01L 2300/0864* (2013.01); *B01L 2300/165* (2013.01); *B01L 2400/0487* (2013.01); *B01L 2400/086* (2013.01); *G01N 33/4915* (2013.01)

(58) Field of Classification Search
CPC .......... Y10T 436/2575; G01N 33/4905; G01N 15/1459; G01N 33/86; G01N 15/12; G01N 2015/1486; G01N 21/03; B01L 2200/146; B01L 2200/16; B01L 2300/0816; B01L 2300/165; B01L 2400/086; B01L 3/502715; B01L 3/502723; B01L 3/50273; B01L 3/502746; B01L 2200/026; B01L 2300/0825; B01L 3/5023; B01L 2400/0406; B01L 2400/0622; B01L 3/502
See application file for complete search history.

(56) References Cited

U.S. PATENT DOCUMENTS

| | | |
|---|---|---|
| 5,164,598 A | 11/1992 | Hillman et al. |
| 5,181,415 A | 1/1993 | Esvan et al. |
| 5,230,866 A | 7/1993 | Shartle et al. |
| 5,236,666 A | 8/1993 | Hulette et al. |
| 5,258,719 A | 11/1993 | Miura et al. |
| 5,272,912 A | 12/1993 | Katsuzaki |
| 5,302,348 A | 4/1994 | Cusack et al. |
| 5,478,751 A | 12/1995 | Oosta et al. |
| 5,591,403 A | 1/1997 | Gavin et al. |
| 5,628,961 A | 5/1997 | Davis et al. |
| 5,646,046 A | 7/1997 | Fischer et al. |
| 5,800,781 A | 9/1998 | Gavin et al. |
| 5,836,360 A | 11/1998 | Gavin et al. |
| 6,084,660 A | 7/2000 | Shartle |
| 6,451,610 B1 | 9/2002 | Gorman et al. |
| 6,575,017 B1 | 6/2003 | Neel et al. |
| 6,750,053 B1 | 6/2004 | Widrig Opalsky et al. |
| 6,915,919 B2 | 7/2005 | Casterlin |
| 6,955,923 B2 | 10/2005 | Hartting |
| 7,005,857 B2 | 2/2006 | Stiene et al. |
| 7,059,352 B2 | 6/2006 | Bohm |
| 7,156,117 B2 | 1/2007 | Bohm |
| 7,497,997 B2 * | 3/2009 | Glezer .................... B01L 9/527 435/7.1 |
| 10,180,419 B2 | 1/2019 | Colella et al. |
| 2002/0123134 A1 * | 9/2002 | Huang .............. B01L 3/502761 435/6.12 |
| 2003/0031594 A1 | 2/2003 | Shartle et al. |
| 2004/0072357 A1 | 4/2004 | Stiene et al. |
| 2004/0109790 A1 | 6/2004 | Shartle et al. |
| 2004/0189311 A1 | 9/2004 | Glezer et al. |
| 2004/0191124 A1 | 9/2004 | Noetzel et al. |
| 2005/0015001 A1 | 1/2005 | Lec et al. |
| 2005/0255601 A1 | 11/2005 | Nippoldt et al. |

\* cited by examiner

CUVETTE-BASED APPARATUS FOR BLOOD COAGULATION MEASUREMENT AND TESTING

CROSS REFERENCE TO RELATED APPLICATION

This application is a continuation of U.S. application Ser. No. 16/210,433 filed Dec. 5, 2018, which is a continuation of U.S. application Ser. No. 13/959,007 filed Aug. 5, 2013, now U.S. Pat. No. 10,180,419, issued on Jan. 15, 2019, which is a continuation application and claims the benefit of U.S. application Ser. No. 13/474,243 filed May 17, 2012, now U.S. Patent Application No. 2013/0017126, issued on Jan. 17, 2013, which is a is a continuation application and claims the benefit of U.S. application Ser. No. 12/503,665 filed on Jul. 15, 2009, now U.S. Patent Application No. 2010/0028207, issued on Feb. 4, 2010, which claims priority to and benefit of U.S. Provisional Application No. 61/081,290 filed on Jul. 16, 2008. The entire contents of each of the above patents and applications are incorporated herein in their entirety by reference for all purposes.

FIELD

The invention relates to apparatus and methods for measuring and testing blood coagulation. More particularly, the invention relates to a cuvette-based apparatus for blood coagulation measurement and testing having automatic volumetric blood sample filling capability.

BACKGROUND

Many people take anticoagulants to maintain the theropedic coagulation time of their blood. Depending upon the person, the peak anticoagulant effect of the anticoagulant may be delayed by many hours and/or days, and the duration of the effect may persist after the peak for another four to five days. Accordingly, it is critical that the people who take anticoagulants closely monitor the coagulation time of their blood, so that they can monitor and adjust the amount of the anticoagulant they are taking.

A common manner of determining the effective amount of anticoagulant in a person's blood is to perform a prothrombin time (PT) test. A PT test measures how long a sample of blood takes to clot. As a result, the anticoagulation or hemostasis level in the blood is directly proportional to the length of time required to form clots.

Many devices and apparatus exist for performing coagulation time measurements and tests. Some of these apparatus are portable and simple enough to operate by a person in his or her home. An example of such an apparatus is describe in U.S. Pat. No. 5,534,226, entitled PORTABLE TEST APPARATUS AND ASSOCIATED METHOD OF PERFORMING A BLOOD COAGULATION TEST, issued to Gavin et al. and assigned to International Technidyne Corporation, the assignee herein. The apparatus described in this patent includes a disposable cuvette and a testing device. In operation, a sample of blood is placed into a cup-like supply reservoir of the cuvette, the blood sample is drawn into the cuvette, and the coagulation time of the blood sample is measured.

A problem associated with such apparatus, is that the volume of the blood sample drawn into the cuvette for measurement and testing is controlled by both the testing device and the sample cup removal techniques. Moreover, the cup-like supply reservoir can be messy to use.

Accordingly, a need exits for an improved apparatus for measuring and testing blood coagulation.

SUMMARY

A cuvette is described herein for use with a blood clot detection instrument. The cuvette comprises a blood sample receptor-inlet and a channel arrangement comprising: at least one test channel for performing a blood clotting time measurement; a sampling channel communicating with the blood sample receptor-inlet and the at least one test channel; a waste channel communicating with the sampling channel; and a vent opening communicating with the sampling channel. At least the sampling channel and the waste channel each has at least one surface portion, a coating, an insert or liner, and any combination thereof, that is hydrophilic. The sampling channel with its at least one surface portion that is hydrophilic, the vent opening and the waste channel with its at least one surface portion that is hydrophilic, coact to automatically draw a requisite volume of a blood sample deposited at the blood receptor-inlet, into the sampling channel. More specifically, air compressed within the blood clot detection instrument, the at least one test channel of the cuvette, and the section of the sampling channel extending beyond the vent opening of the cuvette, coacts with the waste channel to cause the a leading edge of the blood sample drawn into the sampling channel from the blood receptor-inlet, to pull back within the sampling channel and uncover an optical sensor of the blood clot detection instrument. The volume of the blood sample in the sampling channel at the time when the blood sample is pulled back to uncover the optical sensor, equals the requisite volume. The uncovering of the optical sensor activates a pump module of the blood clot detection instrument, which draws the requisite volume of the blood sample into the at least one test channel.

An apparatus is described herein for measuring blood clotting time. The apparatus comprises: a blood clot detection instrument and a cuvette for use with the blood clot detection instrument. The blood clot detection instrument comprises: a pump module and at least one pressure sensor. The cuvette comprises a blood sample receptor-inlet; a channel arrangement comprising: at least one test channel for performing a blood clotting time measurement; a sampling channel communicating with the blood sample receptor-inlet and the at least one test channel; and a waste channel communicating with the sampling channel; and a vent opening communicating with the sampling channel. At least the sampling channel has at least one surface portion, a coating, an insert or liner, and any combination thereof, that is hydrophilic. The sampling channel with its at least one surface portion that is hydrophilic, the vent opening and the waste channel coact to automatically draw a requisite volume of a blood sample deposited at the blood receptor-inlet, into the sampling channel, the requisite volume of blood sample being drawn into the at least one test channel when the pump module of the blood clot detection instrument is activated. The at least one test channel of the cuvette, and the pump module and the at least one pressure sensor of the clot detection instrument, coact to perform a blood clotting time measurement on the requisite volume of the blood sample.

Also described herein is a blood clot detection instrument for automatically measuring blood clotting time of a blood sample contained in a test channel of a cuvette. The blood clot detection instrument comprises a pump module for communicating with the test channel of the cuvette; a pressure sensor, and a central processing unit. The central processing unit executes instructions for operating the pump module in a pressure alternating mode that pumps the blood sample back and forth in a test channel of a cuvette. During clot formation, the viscosity of the blood sample increases and causes a pumping pressure of the pump module to increase over time. The central processing unit executes further instructions for obtaining a baseline pumping pressure from the pressure sensor upon initial operation of the pump module in the pressure alternating mode; obtaining additional pumping pressures over time from the pressure sensor, determining a pumping pressure difference value between each additional pumping pressure and the baseline pumping pressure; comparing each pumping pressure difference value to a predetermined threshold value; and indicating the blood clotting time of the blood sample when the pumping pressure difference value exceeds the predetermined threshold value, the indicated blood clotting time comprising a duration of time extending between the measurement of the additional pumping pressure used for determining the pumping pressure difference value that exceeded the predetermined threshold value and the measurement of the baseline pumping pressure.

BRIEF DESCRIPTION OF THE DRAWINGS

Like reference numbers and designations in the various drawings indicate like elements.

DETAILED DESCRIPTION OF THE INVENTION

Figure 1:
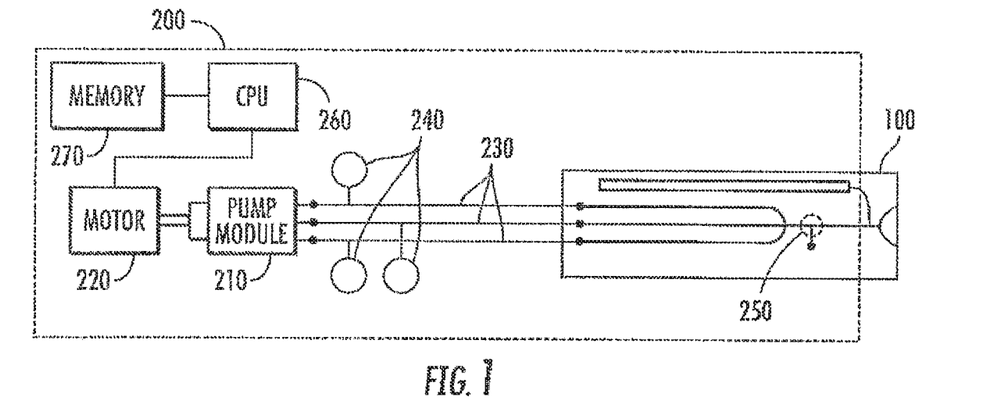
FIG. 1 is a schematic view of an embodiment of a cuvette-based apparatus for measuring blood coagulation or clotting time.

Referring to FIG. 1, there is shown a schematic view of an embodiment of a cuvette-based apparatus 10 for measuring blood coagulation or clotting time. The apparatus 10 generally comprises a disposable cuvette 100 and a blood clot detection instrument 200. The apparatus 10 may be used for measuring blood coagulation time by depositing a sample of blood (whole blood or plasma) onto a specified location of the disposable cuvette 100 and operatively coupling the disposable cuvette 100 to the clot detection instrument 200. The cuvette 100 automatically selects or fills itself with a requisite volume of the blood sample (to be tested) deposited at the specified location of the cuvette 100. The clot detection instrument 200 facilitates automatic mixing of the blood sample with a clotting reagent within the cuvette 100 and automatically measures the clotting time of the selected volume of the blood sample mixed with the clotting reagent within the disposable cuvette 100, without contacting the blood sample. After completion of the measurement, the cuvette 100 may be uncoupled or removed from the clot detection instrument 200 and disposed of. Because the clot detection instrument 200 does not contact the blood sample, another cuvette 100 may be operatively coupled to the clot detection instrument 200 for measuring another blood sample without sterilization or other cleaning of the clot detection instrument 200.

Referring still to FIG. 1, the clot detection instrument 200 comprises a pneumatic pump module 210, a motor 220 for driving the pump module 210, a plurality of tubes 230 extending from the pump module 210 for pneumatically coupling with the cuvette 100, a pressure sensor 240 associated with each tube 230 for measuring the pneumatic pressure within the tube 230, and an optical sensor 250 for optically sensing a sampling channel in the cuvette 100. In one embodiment, the optical sensor 250 comprises, but is not limited, to a LED/photo sensor. The clot detection instrument 200 also comprises, without limitation, a central processing unit 260 (CPU) executing instructions for controlling the operation of the motor 220 and thus the pump module 220 via signals received from the optical sensor 250, and determining clotting time based on the pressures sensed by the pressure sensors 240, a display (not shown) for displaying the measured clotting time or other data related to the measurement, a memory 270 for storing previously performed measurements, and buttons, knobs, and/or switches (not shown) for operating the clot detection instrument 200, controlling the display and/or accessing stored data from the memory 270.

Figure 2A:
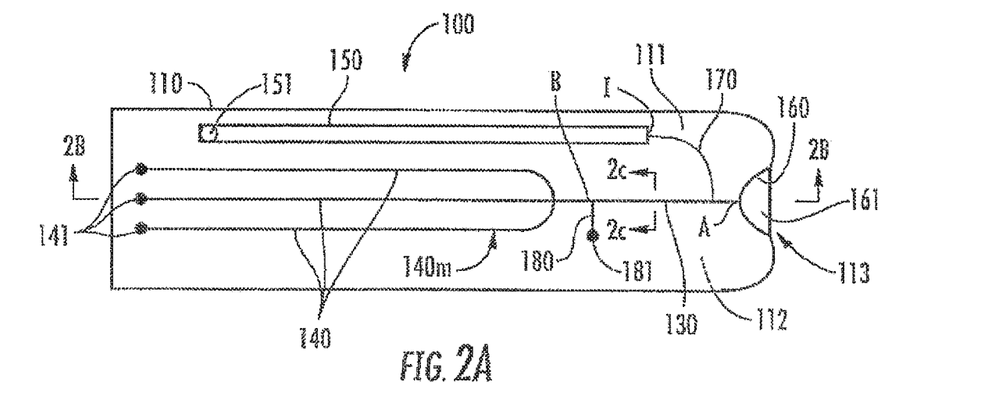
FIG. 2A is a schematic plan view of an embodiment of the disposable cuvette.
Figure 2B:
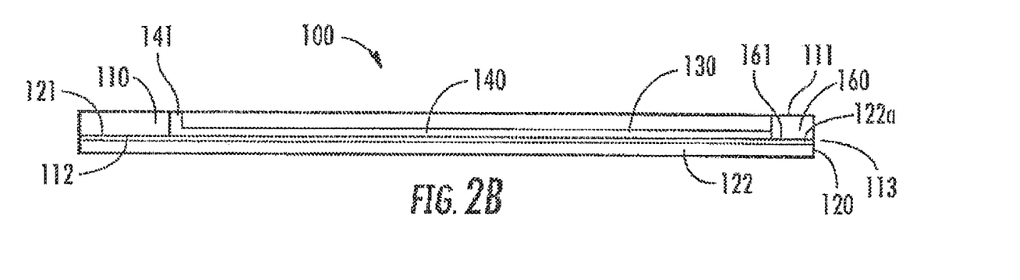
FIG. 2B is a sectional view through line 2B-2B of FIG. 2A.
Figure 2C:
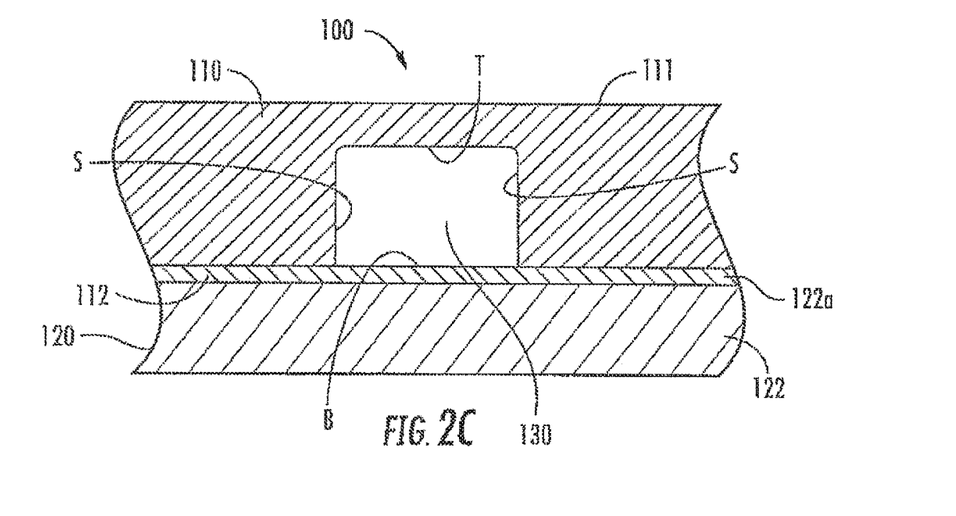
FIG. 2C is a sectional view through line 2C-2C of FIG. 2A.

Referring now to FIGS. 2A-2C, there is collectively shown a schematic plan view of an embodiment of the disposable cuvette 100. The cuvette 100 comprises a substantially planar main body 110 defining generally planar top and bottom surfaces 111, 112. The cuvette main body 110 is typically made from a rigid, transparent hydrophobic or hydrophilic plastic material, using any suitable forming method, such molding. The plastic hydrophobic materials may include, without limitation polystyrene and polytetrafluoroethylene and the plastic hydrophilic materials may include, without limitation, styrene acrylonitrile, acrylonitrile styrene acrylate. The cuvette main body 110 may also be made from other types of rigid, transparent hydrophobic or hydrophilic materials. The cuvette main body 110 includes an arrangement of open channels formed in its bottom surface 112. The open channels are covered and sealed by a thin, substrate 120 that is non-removably attached to the bottom surface 112 of the cuvette body 110 When the cuvette main body 110 is not made from a hydrophilic material or is made from a hydrophobic material, the channels of the channel arrangement each have at least one surface that is hydrophilic, and/or has a hydrophilic coating, and/or has a hydrophilic insert disposed therein (formed, for example, as a tube or liner, thereby fully or partially lining the channel(s)), that facilitates the automatic filling function of the cuvette 100.

In one embodiment, at least a top surface 121 of the thin substrate 120, i.e., the surface in contact with the bottom surface 112 of the cuvette body 110, is hydrophilic or has hydrophilic properties. The hydrophilic properties of the top surface 121 of the substrate 120, facilitates the requisite volumetric selection of the blood sample deposited on the cuvette 100, for coagulation time measurement by the clot detection instrument 200. In other embodiments, requisite volumetric selection of the blood sample is accomplished by forming the cuvette body 110 from a hydrophilic material.

The thin substrate 120, in one embodiment, is a transparent film 122 coated on one side with a layer 122a of clear pressure sensitive hydrophilic adhesive. The layer 122a of hydrophilic adhesive forms the top surface 121 of the substrate 120 and non-removably attaches the substrate 120 to the bottom surface 112 of the cuvette body 110. The transparent film 122 may comprise, in one embodiment, a transparent polyester material.

In an alternative embodiment the transparent film 122 is made from a hydrophilic material. Such a substrate may be attached to the bottom surface 112 of the cuvette body 110 (with the top surface 121 of the substrate 120 mated with the bottom surface 112 of the cuvette body 110) with a layer of adhesive applied to the bottom surface 112 of cuvette body 110. Alternatively, such a substrate may be attached to the bottom surface 112 of the cuvette body 110 using heat scaling methods.

Referring still to FIGS. 2A-2C, the channel arrangement formed in the bottom surface of the cuvette body 110 generally comprises a sampling channel 130, one or more test channels 140 and at least one waste channel 150. A first end 131 of the sampling channel 130 communicates with a sample depositing area 160 formed in a first or front end 113 of the cuvette body 110. The sample depositing area 160 in the front end 113 of the cuvette body 110 and the exposed underlying portion of the substrate 120 form a blood sample receptor and inlet 161 (receptor-inlet 161) on which the entire blood sample is deposited. The sampling channel 130 extends longitudinally in the bottom surface of the cuvette body 110, from the receptor-inlet 161, and merges at its second end with the one or more test channels 140 formed in the bottom surface of the cuvette body 110.

The channel arrangement shown in FIGS. 2A-2C further includes a jumper channel 170 that branches off from the sampling channel 130 just downstream of the receptor-inlet 161 and fluidly connects the waste channel 150 with the sampling channel 130. The terminal end of the waste channel 150 communicates with a waste channel venting aperture 151 formed transversely through the cuvette body 110, which allows "dead" air displaced from within the waste and jumper channels 150, 170 by incoming blood, to be vented to the external environment. The waste channel venting aperture 151 is open to the external environment at the top surface 111 of the cuvette body 110 and closed by the substrate 120 at the bottom surface of the cuvette body 110.

The channel arrangement shown in FIGS. 2A-2C further includes a vent channel 180 that branches off from the sampling channel 130 downstream of the jumper channel 170. The vent channel 180 communicates with a vent opening 181 formed transversely through the cuvette body 110 which allows "dead" air displaced from within the sampling and vent channels 130, 180 by incoming blood to be vented to the external environment. The vent opening 181 is open to the external environment at the top surface 111 of the cuvette body 110 and closed by the substrate 120 at the bottom surface of the cuvette body 110.

As shown in FIG. 2C, the sampling channel 130 (and the jumper, waste and vent channels 170, 150, 180) formed in the bottom surface 112 of the cuvette main body 110 has a smooth top T surface and smooth side surfaces S. The bottom surface B of the sampling channel 130 (and the jumper, waste and vent channels 170, 150, 180) is formed by the top surface 121 (e.g., hydrophilic adhesive layer 122a or the top surface of the hydrophilic film 122) of the substrate 120, which is also smooth.

The cuvette main body 110, in some embodiments, is made from a hydrophobic material. In such embodiments, the sampling, vent, jumper, and waste channels 130, 180, 170, and 150, respectively, each includes at least one surface that is hydrophilic, and/or has a hydrophilic coating, and/or has a hydrophilic insert disposed therein, that facilitates the automatic sample sizing function of the cuvette 100.

In other embodiments, the cuvette main body 110 is made from a hydrophilic material. The one or more test channels 140 in such embodiments, each includes at least one surface that is hydrophobic, and/or has a hydrophobic coating, and/or has a hydrophobic insert disposed therein, where no automatic filling or sample sizing function is required to be performed by the cuvette 100.

The requisite volume of blood sample selected by the cuvette 100 for measurement by the clot detection instrument 200, is obtained from the blood sample deposited on the receptor-inlet 161. The size of this volume is determined by the effective volume of the sampling channel 130. The effective volume of the sampling channel 130 is determined by the width of the sampling channel 130, the height of the sampling channel 130, and length of the sampling channel 130 as measured from point A, which is adjacent to the receptor-inlet 161, to point B, which is adjacent to the vent channel 180. The jumper channel 170, connecting the sampling channel 130 to waste channel 150, delays the filling of the waste channel 150 until the sampling channel 130 is completely filled. The duration of the delay is controlled by an intersection I of the jumper channel 170 and the waste channel 150 and the length and cross-sectional area (CSA) of jumper channel 170 relative to the CSA of the waste channel 150, which insure that blood from the blood sample deposited on the receptor-inlet 161, is drawn into the sampling channel 130 prior to being drawn into the waste channel 150. The delay time is determined by the cross section area and length of the jumper channel 170. The duration of the delay may be increased by lengthening the jumper channel 170, and/or decreasing the cross-sectional area (width and height) of the jumper channel 170 relative to the CSA of the waste channel to increase flow resistant through the jumper channel 170. Thus, during automatic blood sample volume sizing, the intersection I of the jumper channel 170 and the waste channel 150 acts like a resistor. Once a blood sample is applied or deposited in the cuvette's receptor-inlet 161, the blood sample enters the sampling channel 130 and the jumper channel 170 substantially simultaneously. While the blood sample moves forward in the sampling channel 130, it also fills the jumper channel 170, then stops at the intersection I of the jumper channel 170 and the waste channel 150. The sampling channel 130 continues to fill until an equilibrium state is reached. The remaining sample in the receptor-inlet 161 then forces the blood sample into the waste channel 150 from the jumper channel 170. The hydrophilic force of the waste channel 150 picks up and draws off the remaining blood sample in the receptor-inlet 161.

In one embodiment where the cuvette comprises three test channels 140, the sampling channel 130 has a width of about 0.055 inches, a height of about 0.014 inches, and a length of about 0.9 inches; the vent channel 180 has a width of about 0.010 inches, a height of about 0.012 inches, and a length of about 0.140 inches; the jumper channel 170 has a width of about 0.010 inches, a height of about 0.012 inches, and a length of about 0.25 inches; and the waste channel 150 has a width of about 0.066 inches, a height of about 0.014 inches, and length of about 2.24 inches. The three test channels 140 of such a cuvette each has a width of about 0.030 inches and a height of about 0.010 inches. The length of each of the outer two test channels is about 1.69 inches and the inner test channel is about 1.634 inches. The sampling, jumper, waste, and test channel(s) in other embodiments of the cuvette may have other suitable dimensions.

Figure 6A:
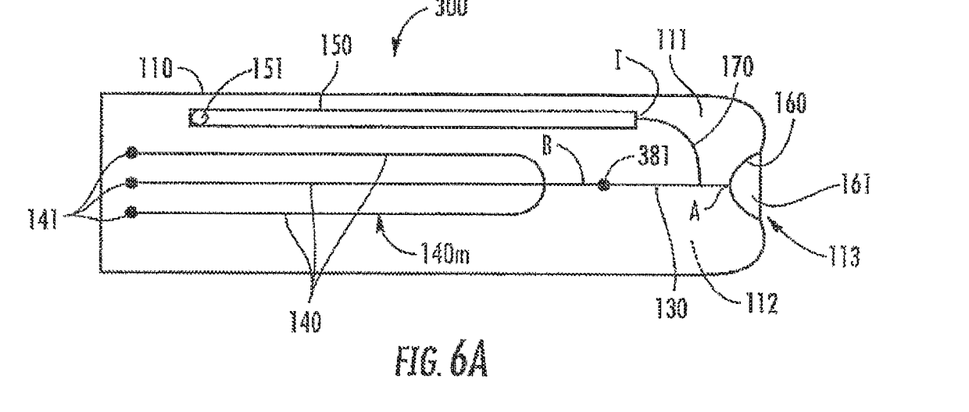
FIG. 6A is a schematic plan view of another embodiment of the disposable cuvette.

FIG. 6A shows an another embodiment of the cuvette, denoted by reference number 300. The cuvette 300 is substantially identical to the cuvette 100 shown in FIG. 2A, except that the vent channel extending between the sampling channel and the vent opening is replaced by a vent opening 381 that directly opens into the sampling channel 130.

Figure 6B:
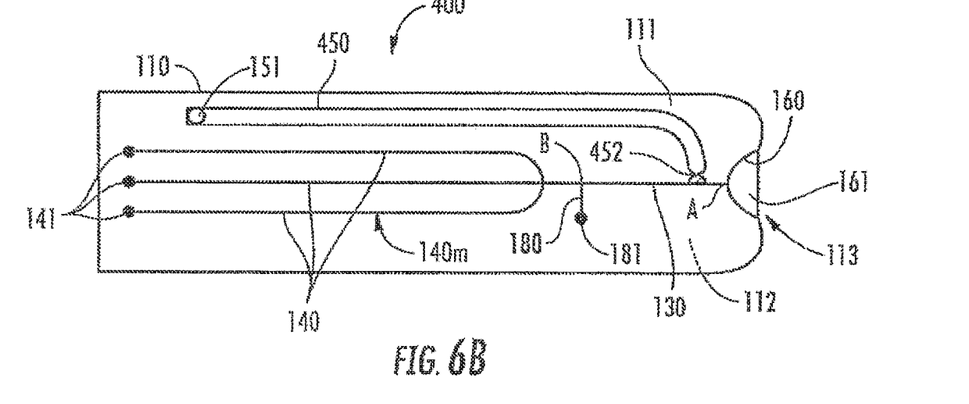
FIG. 6B is a schematic plan view of a further embodiment of the disposable cuvette.

FIG. 6B shows a further embodiment of the cuvette, denoted by reference number 400. The cuvette 400 is substantially identical to the cuvette 100 shown in FIG. 2A, except that the waste channel 450 communicates directly with the sampling channel 130 thereby omitting the jumper channel. In addition, the waste channel 450 includes one or more restrictions 452 located just after the entrance to the waste channel 450 that function to delay filing of the waste channel 450.

Figure 7A:
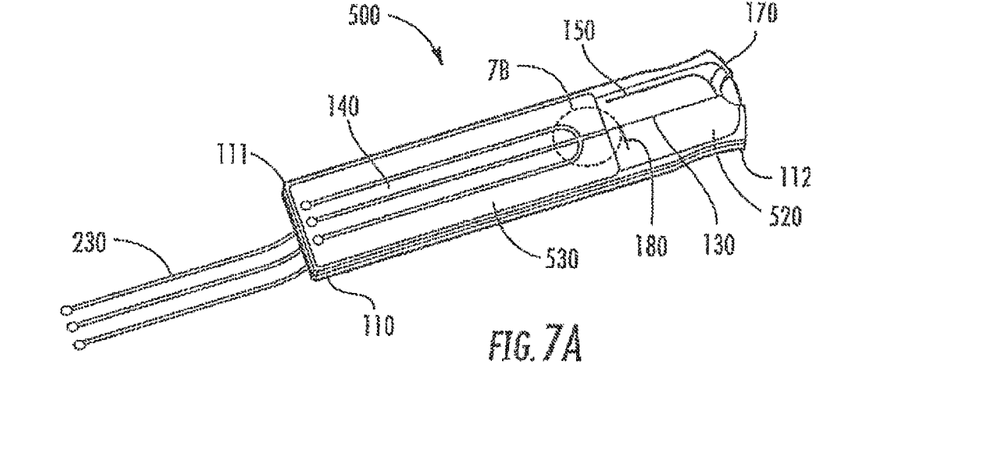
FIG. 7A is a perspective view of a further embodiment of the disposable cuvette.
Figure 7B:
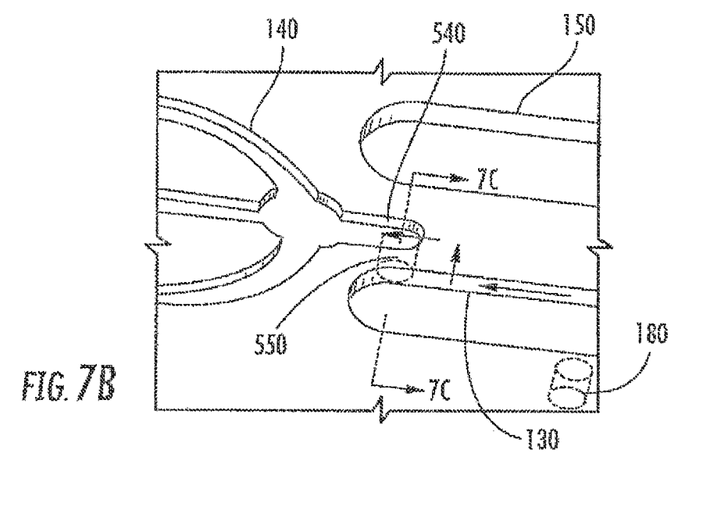
FIG. 7B is an enlarged view of encircled area 7B in FIG. 7A.
Figure 7C:
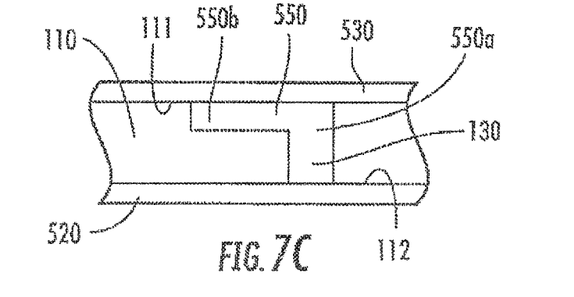
FIG. 7C is a sectional view through line 7C-7C in FIG. 7B.

FIGS. 7A-7C collectively show a further embodiment of a cuvette, denoted by reference number 500. The cuvette 500 is substantially identical to the cuvette 100 shown in FIG. 2A, except that the one or more open test channels 140 are formed in the top surface 111 of the main body 110 instead of in the bottom surface 112 of the main body 110 where the open sampling, vent, jumper, and waste channels 130, 180, 170, 150 are formed. In addition, the open one or more test channels 140 in the top surface 111 of the cuvette main body 110 are covered and sealed by a thin substrate 530 with hydrophobic properties (e.g., the substrate 530 includes a hydrophobic adhesive coating or is a hydrophobic film) that is non-removably attached to the top surface 111 of the cuvette main body 110, and the open sampling, vent, jumper, and waste channels 130, 180, 170, 150 in the bottom surface 112 of the cuvette main body 110 are covered and sealed by a thin, substrate 520 with hydrophilic properties (e.g., the substrate 520 includes a hydrophilic adhesive coating or is a hydrophilic film) that is non-removably attached to the bottom surface 112 of the cuvette body 110. As can be seen in FIGS. 7B and 7C, the sampling channel 103 and an inlet 540 to the one or more test channels 140 are laterally offset from one another. A connecting channel 550 formed in the top surface 111 of the cuvette main body 110, has a first end 550a that communicates with a terminal end of the sampling channel 103 and a second end 550b that communicates with an inlet 540 to the one or more test channels 140. The first end 550a of the connecting channel 550 is covered and sealed by the hydrophillic substrate 520. The remainder of the connecting channel 550 including the second end 550b thereof, is covered and sealed by the hydrophobic substrate 530. The connecting channel 550 transfers the volume of the blood sample precisely collected by the sampling channel 130, to the one or more test channels 140.

In one embodiment, the one or more test channels 140 comprises a branched array of three test channels 140 in a menorah-shaped configuration 140, (visible in FIGS. 2A, 3A, 4, 6A and 6B). The menorah-shaped array of test channels 140m evenly divides the selected volume of blood into three separate blood samples, thereby allowing the cuvette 100 to be used for performing up to three different blood tests. For examples of the blood tests that may be performed in the cuvette, see U.S. Pat. No. 5,534,226, entitled, PORTABLE TEST APPARATUS AND ASSOCIATED METHOD OF PERFORMING A BLOOD COAGULATION TEST, assigned to the International Technidyne Corporation, the assignee herein. The entire disclosure of U.S. Pat. No. 5,534,226 is incorporated herein by reference. The branched array in other embodiments of the cuvette 100 may include two test channels 140 or more than three test channels 140.

Referring still to FIGS. 2A, 3A, 4, 6A and 6B, the terminal or marginal terminal end of each test channel 140 communicates with a drive aperture 141 formed through the cuvette body 110. The drive aperture 141 is open to the external environment at the top surface 112 of the cuvette body 110 and closed by the substrate 120 at the bottom surface of the cuvette body 110. When the cuvette 100 is operatively coupled to the clot detection instrument 200, as shown in FIG. 1, the plurality of tubes 230 extending from the pump module 210 sealingly engage the one or more drive apertures 141 of the cuvette body 110, so that the arrangement of channels and the pneumatic pump module 210 of the clot detection instrument 200 form a pneumatic system when the cuvette 100 is operatively coupled to the clot detection instrument 200.

Figure 3A:
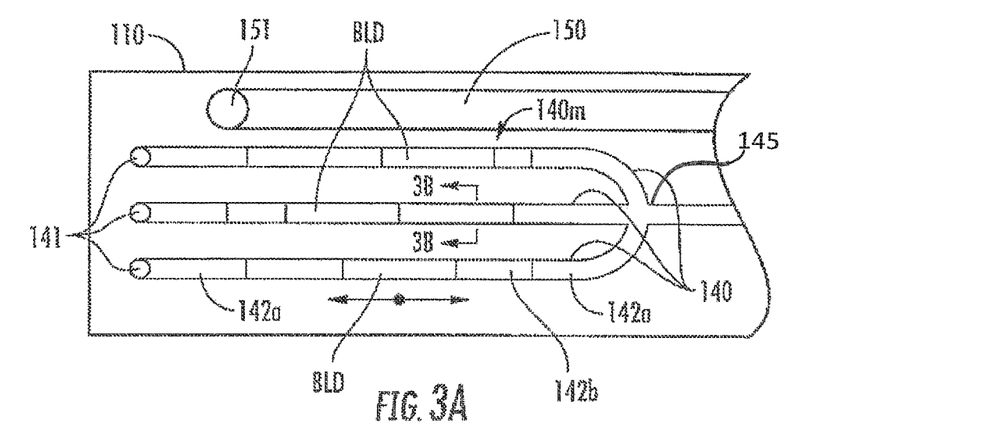
FIG. 3A is an enlarged view of a blood sample testing portion of the disposable cuvette shown in FIG. 2A.
Figure 3B:
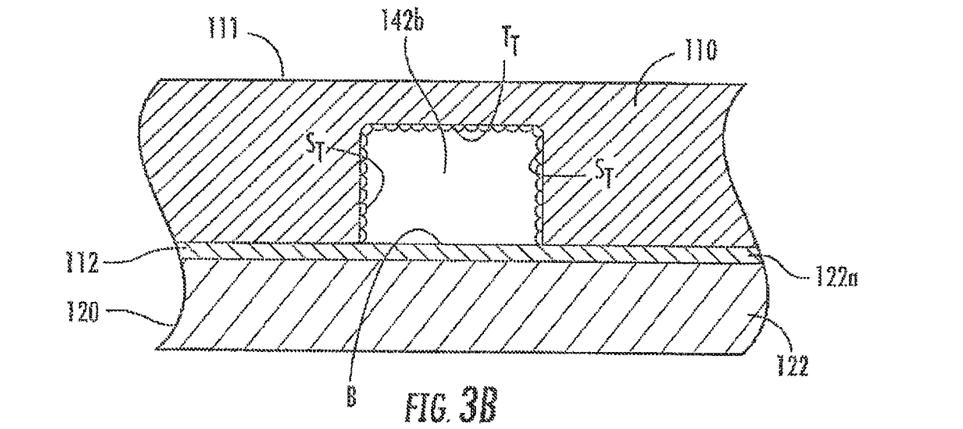
FIG. 3B is a section view through line 3B-3B of FIG. 3A.

Referring now to FIGS. 3A and 3B, each of the test channels 140 formed in the bottom surface of the cuvette body 110 includes end sections 142a with smooth top, side and bottom walls (the bottom wall of each test channel 140 being formed by the smooth top surface 121 of the substrate 120) similar to the top, side and bottom walls of the sampling, jumper and waste channels 130, 170, and 150, and an intermediate section 142b where the top wall $T_T$ and side walls $S_T$ are textured. In one non-limiting embodiment, the texturing may comprise a flat knurl cross-hatch. In other embodiments, the texturing in the intermediate section 142b of one or more of test channels 140 may only be on the top wall or on one or both of the side walls. The length of the textured section is selected so that the blood sample BLD always remains within this section of the test channel 140 during testing. A dehydrated clot promoting reagent (not shown) for triggering and accelerating blood clotting, is disposed in each test channel 140 where the texturing is located. The reagent in each test channel 140 may be the same or different. Therefore, in one embodiment, reagent A may be in each of the test channels. In another embodiment, reagent A may be in two of the test channels and reagent B may be in one of the test channels. In still another embodiment, reagent A may be in one of the test channels, reagent B may be in one of the test channels and reagent C may be in one of the test channels. When the blood sample is drawn into the test channels 140, the reagent rehydrates and mixes with the blood. The textured wall(s) of each test channel 140 improve reagent deposition thereon during manufacture of the cuvette, and increase clotting measurement sensitivity, as the blood sample is reciprocally moved or oscillated therein when measuring of the clotting time of the blood sample, as will be explained further on. In an alternate embodiment, the textured intermediate section of one or more the test channels 140 may be replaced by a restricted area (not shown) where the test channel 140 is narrowed.

Figure 4:
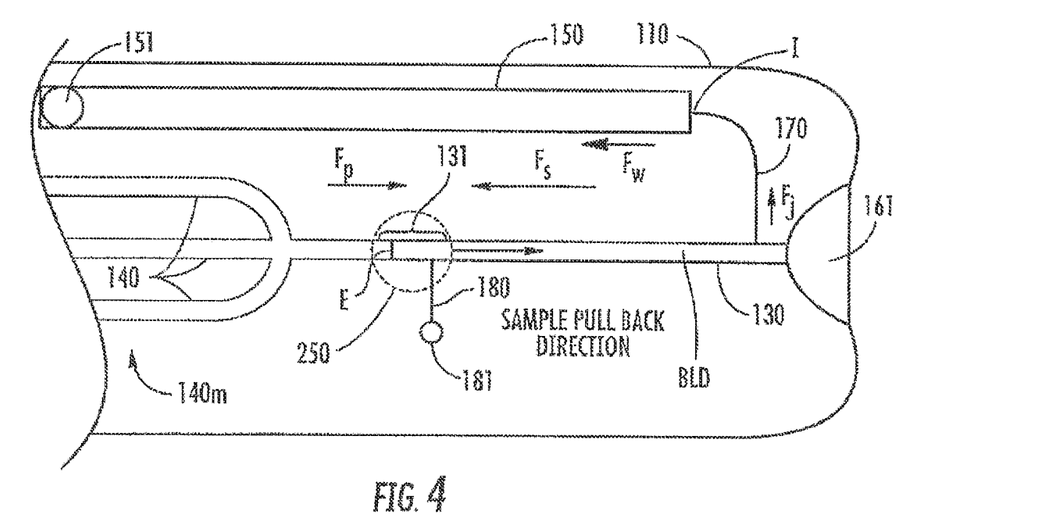
FIG. 4 is an enlarged view of a volumetric blood sampling portion of the disposable cuvette shown in FIG. 2A.

The automatic volumetric filling function of the cuvette 100 will now be described in greater detail with reference to FIG. 4. Prior to volumetric filling, the cuvette 100 must be operatively coupled to the clot detection instrument 200 such that the plurality of tubes 230 extending from the pump module 210 of the clot detection instrument 200 sealingly engage the one or more drive apertures 141 of the cuvette body 110, thereby creating a pneumatic system formed by the arrangement of channels of the cuvette 100 and the pneumatic pump module 210 of the clot detection instrument 200, as shown in FIG. 1. The automatic volumetric filling function commences when a blood sample is deposited onto the receptor-inlet 161 of the cuvette 100. The blood sample may be deposited on the receptor-inlet 161 by finger after a fingerstick, a needle, a dropper, a pipette, a capillary tube, or any other suitable depositing device. Since at least a portion of the sampling channel 130 is hydrophilic, a force $F_s$, is generated by the hydrophilicity of this portion, which initially draws the blood sample deposited on the receptor-inlet 161 into the sampling channel 130 until the entire vent channel 180 becomes filled. The dead air in the vent channel 180 and the section of the sampling channel 130 extending between the receptor-inlet 161 and the vent channel 180, is vented through the vent opening 181 of the vent channel 180 as the blood BLD fills this section of the sampling channel 130, and the vent channel 180. The blood drawn into the vent channel 180 seals the vent opening 181. At the same time the jumper channel hydrophilicity force $F_j$ draws blood into the jumper channel. Once the vent channel 180 has been filled, the force $F_s$ continues to draw more blood from the blood sample deposited on the receptor-inlet 161 into the sampling channel 130 such that the blood BLD in the sampling channel 130 overshoots the vent channel 180 and covers the optical sensor 250 of the clot detection instrument 200, which lies under or over section or area 131 of the sampling channel 130. The blood BLD which overshoots the vent channel 180 compresses the dead air volume contained within the section of the sampling channel 130 extending beyond the vent channel 180, the test channels 140, and the tubes 230 of the clot detection instrument 200, and the pump module 210, because $F_s > F_p$ and $F_w \ll F_s$, where $F_p$ is the pressure of the compressed dead air volume, and $F_w$ is the hydrophilicity force generated by at least a portion of the waste channel 150 that is hydrophilic. Blood stops flowing in the sampling channel 130 towards the test channels 140 when an equilibrium state $F_s = F_p + F_w$ is achieved therein.

After the equilibrium state has been reached, blood that has been delayed by the the jumper channel/waste channel intersection I and the jumper channel 170, reaches the waste channel 150. The waste channel 150 generates a force $F_w$, that increases to a value proportional to the line of contact between the blood and the hydrophilic surface, which first pulls additional blood remaining in the receptor-inlet 161 into the waste channel 150. As the waste channel 150 fills with excess blood sample BLD, dead air disposed therein and displaced by the incoming blood BLD is vented to the external environment through the waste channel venting aperture 151. Once the remaining blood sample drawn off from the receptor-inlet 161, force $F_w + F_p$ becomes greater than $F_s$, and therefore, the leading edge E of the blood BLD in the sampling channel 130 starts pulling back towards the vent channel 180.

The leading edge E of the blood BLD in the sampling channel 130 continues to be pulled back by force $F_w + F_p$ and uncovers the optical sensor 250. The volume of the blood sample BLD disposed in the sampling channel 130 at the moment the optical sensor 250 is uncovered, is the requisite volume. Consequently, the pump module 210 of the clot detection instrument 200 is immediately activated by the uncovered optical sensor 250 and draws this requisite volume of blood sample BLD into the test channels 140 such that the blood sample BLD is disposed in the sections of the test channels 140 that are textured. The ratio of force $F_w$ to force $F_s$ determines the sample pull back speed. Generally, a wider waste channel 150 has stronger pull back. In one, non-limiting embodiment, the ratio of force $F_w$ to force $F_s$ equals 1.2. One of ordinary skill in the art will recognize that the forces described above may be adjusted by the material properties of the cuvette body 110, substrate 120, size and/or geometry of the plurality of channels. The blood sample over shoot and pull back functions of the sampling channel 130 may also be adjusted and controlled by the volume of dead air in the tubes 230 and pump module 210 of the clot detection instrument 200.

Figure 5:
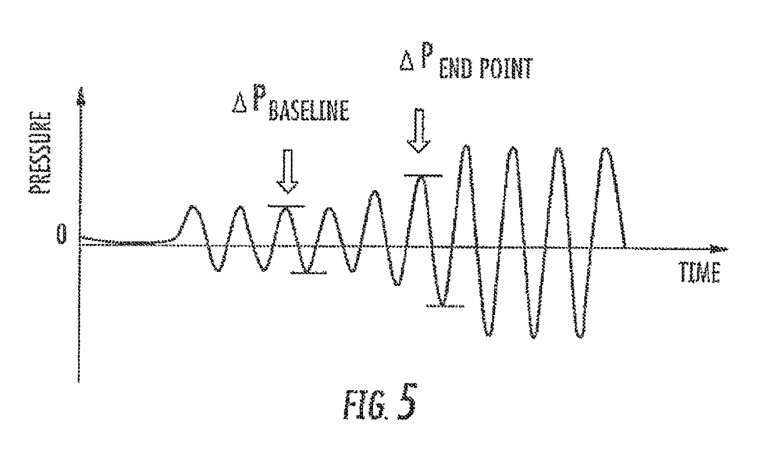
FIG. 5 is a pressure profile and clot detection graph.

The automatic blood clot testing function of the cuvette 100 will now be described in greater detail with reference to FIGS. 3A and 5. After the pump module 210 has drawn the blood sample into one or more test channels 140 of the cuvette 100, the pump module 210 automatically switches into a pumping mode where it alternately creates positive and negative pressures in the test channels 140 of the cuvette 100. The alternating positive and negative pressures (pumping pressure) reciprocally moves the blood samples BLD back and forth across textured sections (or restricted areas) of the one or more test channels 140, thereby mixing the blood sample with dehydrated reagent, as shown in FIG. 3A. As the reagent rehydrates and mixes with the blood sample BLD, it triggers and accelerates the blood clotting cascade. Fibrin formation within the blood sample BLD causes the viscosity of the blood sample BLD to increase with time. The viscosity increase may be detected, in one embodiment, by measuring the pumping pressure within each test channel 140 over time. As shown in the graph of FIG. 5, the pumping pressure starts at an initial pumping pressure value (pumping pressure baseline $\Delta P_{baseline}$) and increases with time, as the viscosity of the blood increases during clotting. The pressure sensors 240 of the blood clot detection instrument 200, measure the pump pressure over time and the CPU 260 of the clot detection instrument 200 compares this data to the initial pressure baseline $\Delta P_{baseline}$. The clotting time of the blood sample may be determined when pressure value is greater than or equal to a preset threshold. In one embodiment, the clotting time is, $$\Delta P_{end\ point} - \Delta P_{baseline} \geq \text{threshold},$$

where $\Delta P_{end\ point}$ is the clotting end point peak to peak pressure.

The preset threshold may be fixed or dynamic. In one embodiment, a dynamic threshold may be, $$\Delta P_{baseline} + (0.3 \times \Delta P_{baseline}).$$

In general, the hydrophilicity of the one or more test channels 140 will aid the robust automatic volumetric blood sample filling function of the cuvette 100, while impeding the clotting performance of the cuvette 100. Appropriately balancing the test channel 140 dimensions, geometry, degree of texturing/restriction size, and the hydrophilic properties of the cuvette body 110 and substrate 120, will provide the cuvette 100 with requisite blood clotting performance.

The pump profile of the pump module 210, i.e., pumping speed and stroke, may also affect clotting performance. For example, a pump speed greater than 20 millisecond (ms) per pump step, equivalent to 20 ul per sec in test channel or a pump stroke greater than 55 steps, equivalent to 0.044, may increase the chance of deforming a weak clot (International Normalized Ratio >4.0), which may in turn, result in lower clot detection precision. In one embodiment, the pump profile is 40 ms per pump step and 36 steps per pump direction (generates positive and negative pressures).

While exemplary drawings and specific embodiments have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the art without departing from the scope of the present invention as set forth in the claims that follow and their structural and functional equivalents.

What is claimed is:

1. A method for measuring blood clotting time, the method comprising:
    coupling a cuvette to a blood clot detection instrument, wherein the blood clot detection instrument comprises:
        a pump module; and
        at least one pressure sensor; and
    wherein the cuvette comprises:
        a main body including:
            i) a blood sample receptor-inlet;
            ii) a channel arrangement comprising:
                a) at least one test channel for communicating with the pump module when the cuvette is operatively coupled to the clot detection instrument;
                b) a sampling channel fluidically coupled to the at least one test channel and to a sample deposit area at the blood sample receptor-inlet, at least a portion of the sampling channel having a hydrophilic surface such that blood is automatically drawn from the blood sample-receptor inlet;
                c) a vent opening fluidically coupled to the sampling channel, the vent opening configured to vent air from the sampling channel as the sampling channel fills with blood, a predetermined sample volume defined by a volume of the sampling channel between the blood sample-receptor inlet and the vent opening; and
                d) a waste channel fluidically coupled to the sampling channel between the blood sample receptor-inlet and the vent opening, a flow restriction at an intersection of the waste channel and the sampling channel impeding blood from flowing into the waste channel until the sampling channel is filled to the vent opening such that the sampling channel automatically fills with the predetermined sample volume.

2. The method of claim 1, wherein the channel arrangement further comprises a vent channel connecting the vent opening with the sampling channel.

3. The method of claim 1, further comprising performing automatic volumetric filling of the cuvette.

4. The method of claim 3, wherein the automatic volumetric filling of the cuvette comprises:
    commencing the automatic volumetric filling when a blood sample is deposited onto the blood sample receptor-inlet of the cuvette.

5. The method of claim 4, wherein the blood sample is deposited onto the blood sample receptor-inlet by one of a finger after a fingerstick, a needle, a dropper, a pipette, a capillary tube, or any other suitable depositing device.

6. The method of claim 3, wherein a force generated by a hydrophilic portion of the sampling channel initially draws the blood sample into the sampling channel until the vent channel becomes filled.

7. The method of claim 3, wherein dead air in the vent channel and a section of the sampling channel extending between the blood sample receptor-inlet and the vent channel is vented through the vent opening of the vent channel as the blood sample fills the vent channel and a section of the sampling channel extending between the blood sample receptor-inlet and the vent channel.

8. The method of claim 6, wherein the force generated by a hydrophilic portion of the sampling channel draws from the blood sample deposited on the receptor-inlet into the sampling channel such that the blood sample in the sampling channel overshoots the vent channel and covers an optical sensor of the blood dot detection instrument once the vent channel has been filled.

9. A method for measuring blood clotting time, the method comprising:
    performing an automatic blood clotting test using a cuvette coupled to a blood clot detection instrument, wherein the blood clot detection instrument comprises:
        a pump module; and
        at least one pressure sensor; and
    wherein the cuvette comprises:
        a main body including:
            i) a blood sample receptor-inlet;
            ii) a channel arrangement comprising:
                a) at least one test channel for communicating with the pump module when the cuvette is operatively coupled to the clot detection instrument;
                b) a sampling channel fluidically coupled to the at least one test channel and to a sample deposit area at the blood sample receptor-inlet, at least a portion of the sampling channel having a hydrophilic surface such that blood is automatically drawn from the blood sample-receptor inlet;
                c) a vent opening fluidically coupled to the sampling channel, the vent opening configured to vent air from the sampling channel as the sampling channel fills with blood, a predetermined sample volume defined by a volume of the sampling channel between the blood sample-receptor inlet and the vent opening; and
                d) a waste channel fluidically coupled to the sampling channel between the blood sample receptor-inlet and the vent opening, a flow restriction at an intersection of the waste channel and the sampling channel impeding blood from flowing into the waste channel until the sampling channel is filled to the vent opening such that the sampling channel automatically fills with the predetermined sample volume.

10. The method of claim 9, wherein the at least one test channel includes a dehydrated clot promoting reagent for triggering and accelerating blood clotting.

11. The method of claim 10, wherein the pump module automatically switches into a pumping mode where the pump module alternatively creates positive and negative pressures in the at least one test channel of the cuvette when the pump module draws the blood sample into the at least one test channel of the cuvette.

12. The method of claim 11, wherein the blood sample rehydrates the dehydrated clot promoting reagent and mixes with the dehydrated clot promoting reagent in the at least one test channel.

* * * * *